United States Patent [19]
Tsunakawa et al.

[11] Patent Number: 5,466,450
[45] Date of Patent: Nov. 14, 1995

[54] ANTIVIRAL ANTIBIOTIC BU-4224V

[75] Inventors: Mitsuaki Tsunakawa, Kamiooka; Tetsuro Yamasaki, Kohoku; Koji Tomita, Tokyo; Osamu Tenmyo, Midori, all of Japan

[73] Assignee: Bristol-Myers Squibb Co., New York, N.Y.

[21] Appl. No.: 95,435

[22] Filed: Jul. 20, 1993

Related U.S. Application Data

[62] Division of Ser. No. 559,864, Jul. 27, 1990, Pat. No. 5,256,646.

[51] Int. Cl.$^6$ ............................................. A61K 35/00
[52] U.S. Cl. ..................... 424/118; 424/119; 435/74; 435/822; 514/25; 514/32; 536/7.1; 536/16.8; 536/17.9; 536/18.1
[58] Field of Search ...................... 424/118, 119; 536/7.1, 16.8, 17.9, 18.1; 514/25, 32; 435/74, 822

[56] References Cited

U.S. PATENT DOCUMENTS

| | | | |
|---|---|---|---|
| 4,369,178 | 1/1983 | Yamamura et al. | 424/177 |
| 4,908,353 | 3/1990 | Yamamoto et al. | 514/19 |

*Primary Examiner*—Douglas W. Robinson
*Assistant Examiner*—Elli Peselev
*Attorney, Agent, or Firm*—Aldo A. Algieri

[57] ABSTRACT

A novel antibiotic complex designated BU-4224V produced by fermentation of Kibdelosporangium albatum sp. nov. Strain R761-7. The complex may be separated chromatographically into bioactive components designated BU-4224V A, $B_1$, $B_2$, and C. The components BU-4224V $B_1$ and $B_2$ display both antiviral and antimicrobial activity, while component BU-4224V A has antimicrobial activity and component BU-4224V C has antiviral activity.

5 Claims, 10 Drawing Sheets

ANTIVIRAL ANTIBIOTIC BU-4224V

This application is a division, of application Ser. No. 07/559,864, filed Jul. 27, 1990 U.S. Pat. No. 5,256,646.

BACKGROUND OF THE INVENTION

The present invention relates to a novel antibiotic complex having antiviral and/or antimicrobial activity, to its production, recovery and separation into four bioactive components, and to a pharmaceutical composition thereof.

SUMMARY OF THE INVENTION

There is provided by the present invention a new antibiotic complex designated BU-4224V, said complex being produced by cultivating a BU-4224V-producing strain of *Kibdelosporangium albatum*, preferably strain *Kibdelosporangium albatum*, sp. nov. strain R761-7, or variants or mutants thereof, in an aqueous fermentation culture nutrient medium containing assimilable sources of nitrogen and carbon under submerged aerobic conditions until a substantial amount of the antiviral antibiotic complex BU-4224V is produced by the organism in the fermentation culture nutrient medium and subsequently, recovering the BU-4224V complex from the culture medium. The BU-4224V complex contains four bioactive components designated BU-4224V A, BU-4224V $B_1$, BU-4224V $B_2$, and BU-4224V C which may be separated by conventional chromatographic procedures.

The BU-4224V A, $B_1$, $B_2$, and C components exhibit antiviral activity against herpes simplex virus type 1 (HSV-1) in the dye uptake assay and the plaque reduction assay, and/or antimicrobial activity in the agar dilution method.

DETAILED DESCRIPTION OF THE INVENTION

Figure 1A:
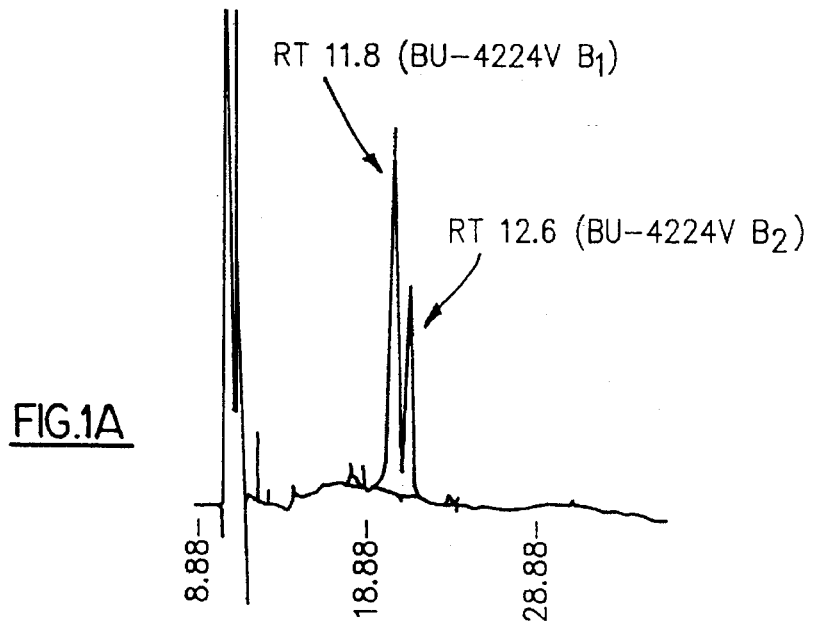
FIG. 1 shows the HPLC chromatograms of the BU-4224V components.

This invention relates to novel antiviral and/or antimicrobial antibiotics designated herein as BU-4224V A, $B_1$, $B_2$, and C and to their preparation by fermentation of certain strains of *Kibdelosporangium albatum*, most particularly *Kibdelosporangium albatum* sp. nov. Strain R761-7.

Strain R761-7 was isolated from a soil sample collected in Mindanao Island, the Philippines. A biologically pure culture of this strain was deposited with the American Type Culture Collection, Rockville, Md. under the accession number ATCC 55061.

The cultural and physiological characteristics of the strain were examined by the methods of Shirling & Gottlieb[1] and Shearer et al.[2] Diagnostic amino acid and sugar in the whole cell hydrolysate were analyzed by the methods of Lechevalier.[3] The phospholipids were identified by the descriptions of Lechevalier et al.[4] The menaquinone samples were prepared by the procedures of Collins et al,[5] and analyzed with a mass spectrometer. The detection of mycolate and the glycolate test were carried out by the methods of Minnikin et al,[6] and Uchida & Aida,[7] respectively.

The Microorganism

The actinomycete strain R761-7 which produces antiviral and/or antimicrobial antibiotics BU-4224V A, $B_1$, $B^2$, and C was isolated from a soil sample collected in the Philippines. The morphology, cultural and physiological characteristics and chemotaxonomy of strain R761-7 indicated that the strain is classified into the genus Kibdelosporangium. Based on the direct or descriptive comparisons of the strain to known species of the genus, the strain was designated *Kibdelosporangium albatum* sp. nov.

Morphology

Strain R761-7 is an aerobic, gram-positive, non-acid-fast filamentous organism that forms well-branched substrate and aerial mycelia. The substrate mycelium exhibits varying degrees of fragmentation. The aerial mycelium bears long straight chains of spores and many sporangiumlike globular bodies (8~20 μm in diameter). The spores are cylindrical (0.4×0.8~2 μm), and have smooth surface without distinct sheath. The sporangiumlike globules with membranous envelope contain irregularly curved, branched hyphae, but not spores, and have rugose surface. Germination occurs directly from these globules. Motile cells are not observed.

Cultural characteristics

Aerial mycelium is formed on most agar media, and is white or yellowish white in mass-color. The substrate mycelium is colorless to yellowish brown or orange yellow. Melanin and other distinct pigments are not produced. The cultural characteristics are shown in Table 1.

Physiological characteristics

Gelatin and potato starch are hydrolyzed. Milk is coagulated and peptonized. NaCl tolerance is seen at 4% but not at 5% or more. The growth occurs between 17° C. and 45° C. No growth is observed in 14° C. and 48° C. The physiological characteristics are shown in Table 2.

Chemotaxonomy

Whole cell hydrolysate contains meso-diaminopimelic acid as the diagnostic amino acid. Whole cell-sugar consisted of rhamnose, ribose, arabinose, glucose and galactose. Madurose is not detected. The phospholipids contain two phosphatidylethanolamines, phosphatidylglycerol and phosphatidylinositol. Thus, strain R761-7 has a type IV cell wall with a sugar pattern A, and a type P-II phospholipid. The major menaquinone is MK-9 ($H_4$). Mycolate is absent. Glycolate test is negative (N-acyl type of peptidoglycan: acetyl).

Taxonomic position

Based on the micro-morphological study by photomicroscopy and scanning electron microscopy, the sporangiumlike structure of strain R761-7 is differentiated from the sporangium of Streptosporangium and Spirillospora, from the pseudosporangium of Actinosporangium and Actinomadura, and also from the sclerotium of Chainia.

The chemotaxonomy of strain R761-7 revealed that the cell chemistry of strain R761-7 is closely related to genera Amycolatopsis[8] and Kibdelsporangium[2] but is differentiated from the other hither-to described, spore-forming genera of actinomycetes. The morphology and chemotaxonomy of strain R761-7 is consistent with those of the genus Kibdelosporangium; that is Kibdelosporangium is characterized by the formations of hyphi-enveloping sporangiumlike structure as well as spore chain on the aerial mycelium, and by the type IV-A cell wall, type P-II phospholipids, MK-9 ($H_4$) major menaquinone and lack of mycolate. Strain R761-7 is also similar to the genus in the cultural characteristics, e.g. the formation of white aerial mycelia and the moderate or good growth both on the natural organic media and chemically defined media.

Thus, strain R761-7 was classified into the genus Kibdelosporangium, which includes only two species and one subspecies, (E. aridum,[2,9] K. philippinense,[10] and K. aridum subsp. largum[11]). The direct or descriptive comparison of the characteristics of strain R761-7 to those of the two known species of genus Kibdelosporangium are shown in Table 2. Strain R761-7 is different from all known species of Kibdelosporangium in the lack of melanin formation in any of ISP media nos. 1, 6 and 7, the hydrolysis of starch, the acid formation from adonitol, and the lack of acid formation from D-melezitose, melibiose and α-methyl-D-glucoside.

The comparative considerations between strain R761-7 and two known species of Kibdelosporangium led us to classify this strain as a new species of the genus. Hence, the designation, *Kibdelosporangium albatum* sp. nov. is proposed for the strain. The type strain is No. R761-7 which is single isolate.

TABLE 1

Cultural characteristics of strain R761-7

| Medium | Growth | Aerial mycelium | Substrate mycelium | Diffusible pigment |
|---|---|---|---|---|
| Sucrose-nitrate agar (Czapek-Dox agar) | Good | Moderate; pale yellow (89) | Moderate orange yellow (71) | Light yellowish brown (76) |
| Tryptone-yeast extract broth (ISP No. 1) | Moderate, pellicle, not turbid | None | Light yellowish brown (76) | None |
| Yeast extract-malt extract agar (ISP No. 2) | Good | Poor; white | Deep yellow (85) | None |
| Oatmeal agar (ISP No. 3) | Moderate | Poor; white to light yellow (86) | Colorless to light brown (57) | None |
| Inorganic salts-starch agar (ISP No. 4) | Good | Moderate; yellowish white (92) | Moderate yellowish brown (77) | None |
| Glycerol-asparagine agar (ISP No. 5) | Moderate | Moderate; yellowish white (92) | Brilliant orange yellow (67) | None |
| Peptone-yeast extract-iron agar (ISP No. 6) | Moderate | Moderate; white | Vivid yellow (82) | Pale yellow (89) |
| Tyrosine agar (ISP No. 7) | Moderate | Moderate; white | Brilliant orange yellow (67) | Light orange yellow (70) |
| Glucose-asparagine agar | Poor | Poor; white | Pale yellow (89) | None |

Observation after incubation at 28° C. for 3 weeks
Color name, used: ISCC-NBS color-name charts.

TABLE 2

Physiological characteristics of strain R761-7 in comparison with two species of genus Kibdelosporangium

| | Strain R761-7 | K. aridum | K. philippinense |
|---|---|---|---|
| Acid from: | | | |
| Adonitol | + | − | − |
| L-Arabinose | + | + | − |
| D-Cellobiose | + | + | + |
| Dextrin | + | + | − |
| Dulcitol | − | − | − |
| i-Erythritol | − | − | − |
| D-Fructose | + | + | + |
| D-Galactose | + | + | + |
| D-Glucose | + | + | + |
| Glycerol | + | + | + |
| i-Inositol | + | + | + |
| Lactose | +(w) | + | + |
| Maltose | + | + | + |
| D-Mannitol | + | + | + |
| D-Mannose | + | + | + |
| D-Melezitose | − | + | + |
| Melibiose | − | + | + |
| α-Methyl-D-glucoside | − | + | + |
| Raffinose | − | + | − |
| L-Rhamnose | + | + | + |
| D-Ribose | + | + | + |
| Salicin | + | v | − |
| D-Sorbitol | − | − | − |
| L-Sorbose | − | − | − |
| Sucrose | + | + | − |
| Trehalose | + | + | + |
| D-Xylose | + | + | + |
| Production of: | | | |
| Nitrate reductase | − | − | + |
| Catalase | + | + | + |

TABLE 2-continued

Physiological characteristics of strain R761-7 in comparison with two species of genus Kibdelosporangium

|  | Strain R761-7 | K. aridum | K. philippinense |
|---|---|---|---|
| Hydrogen sulfide | + | + | + |
| Melanin | − | + | + |
| Hydrolysis of: |  |  |  |
| Potato starch | + | − | − |
| Gelatin | + | + | + |
| Utilization of: |  |  |  |
| Benzoate | − | − | − |
| Citrate | − | + | + |
| Mucate | − | − | UD |
| Succinate | + | + | + |
| Tartrate | − | − | − |
| Decomposition of: |  |  |  |
| Adenine | − | − | − |
| Casein | + | + | + |
| L-Tyrosine | + | + | + |
| Hypoxanthine | − | − | + |
| Xanthine | − | − | − |
| Cellulose | − | − | − |
| Urea | + | + | + |
| Esculin | + | + | + |
| Hippurate | + | + | + |
| Growth at/in: |  |  |  |
| 10° C. | − | + | − |
| 15° C. | ± | + | − |
| 42° C. | + | + | − |
| 45° C. | − | Trace | − |
| Lysozyme broth | +(w) | − | + |
| 4% NaCl | + | + | − |
| 5~7% NaCl | − | + | − |
| 8% NaCl | − | − | − |

UD: undescribed
(w): weak
*K. aridum* subsp. *largum* ATCC 39922 is reported to be not differentiated physiologically from *K. aridum* ATCC 39323 (J. Antibiotics 39: 1386–1394, 1986).

Fermentation

The BU-4224V antibiotics of the present invention are produced by cultivating a BU-4224V producing strain of *Kibdelosporangium albatum*, preferably *Kibdelosporangium albatum*, ATCC 55061, or a mutant or variant thereof, under submerged aerobic conditions in an aqueous nutrient medium. The producing organism is grown in a nutrient medium containing an assimilable carbon source, for example an assimilable carbohydrate. Examples of suitable carbon sources include lactose, glycerol, sucrose, corn starch, glucose, mannose, fructose, cellobiose, trehalose, mannitol and xylose. The nutrient medium should also contain an assimilable nitrogen source such as fish meal, peptones, soybean meal, peanut meal, cotton seed meal and corn steep liquor. Nutrient inorganic salts may also be incorporated in the medium and such salts may comprise any of the usual salts capable of providing sodium, potassium, ammonium, calcium, phosphate, sulfate, chloride, bromide, nitrate, carbonate or like ions.

Production of BU-4224V may be effected at any temperature conductive to satisfactory growth of the organism, i.e., approximately 17°–45° C. and is conveniently carried out at a temperature of about 28° C. Ordinarily, optimum production is obtained after incubation period of about 4–6 days. The fermentation may be carried out in flasks and in laboratory or industrial fermentors of various capacities. When tank fermentation is to be carried out, it is desirable to produce a vegetative inoculum in a nutrient broth by inoculating the broth culture with a slant or soil culture or a lyophilized culture of the organism. The medium in which the vegetative inoculum is produced can be the same as, or different from, that utilized in the tank for the production of the new compounds of the present invention as long as it is such that a good growth of the microorganism is obtained.

Production of BU-4224V can be followed during the course of fermentation by testing samples of the broth or extracts of the mycelial solids for activity against organisms known to be sensitive to the compounds of the present invention or by an in vitro cytotoxicity assay.

Figure 1B:
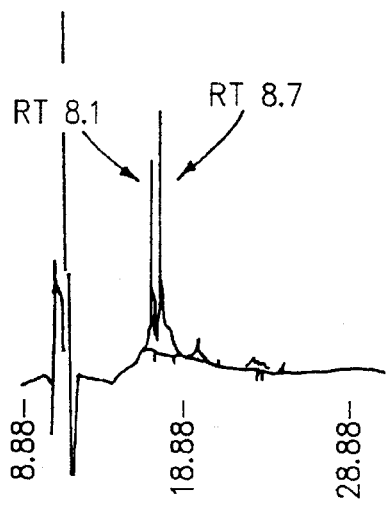
Figure 1C:
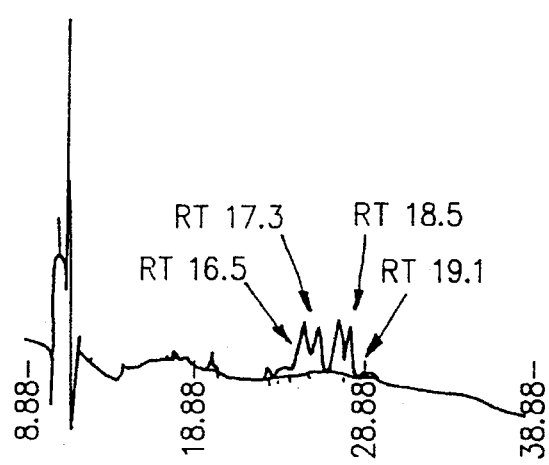

When fermentation is complete, the components are recovered from the fermentation broth and separated by extraction with a suitable organic solvent followed by a series of column chromatographies. Example 2 below illustrates specific procedures for obtaining the components A, $B_1$, $B_2$, and C. FIG. 1 shows the HPLC chromatograms of components A, $B_1$, $B_2$, and C.

As is the case with other microorganism, the characteristics of the new BU-4224V-producing strain of the present invention strain R761-7, (ATCC 55061), are subject to variation. Recombinants, variants and mutants of strain R761-7 (ATCC 55061) may be obtained by treatment with various known mutagens such as ultraviolet rays, X-rays, high frequency waves, radioactive rays and chemicals. Natural and induced variants, mutants and recombinants of strain R761-7, (ATCC 55061) which retain the characteristic of producing BU-4224V are intended to be encompassed by the present invention.

Physico-chemical properties of BU.4224V $B_1$ and $B_2$

Figure 2:
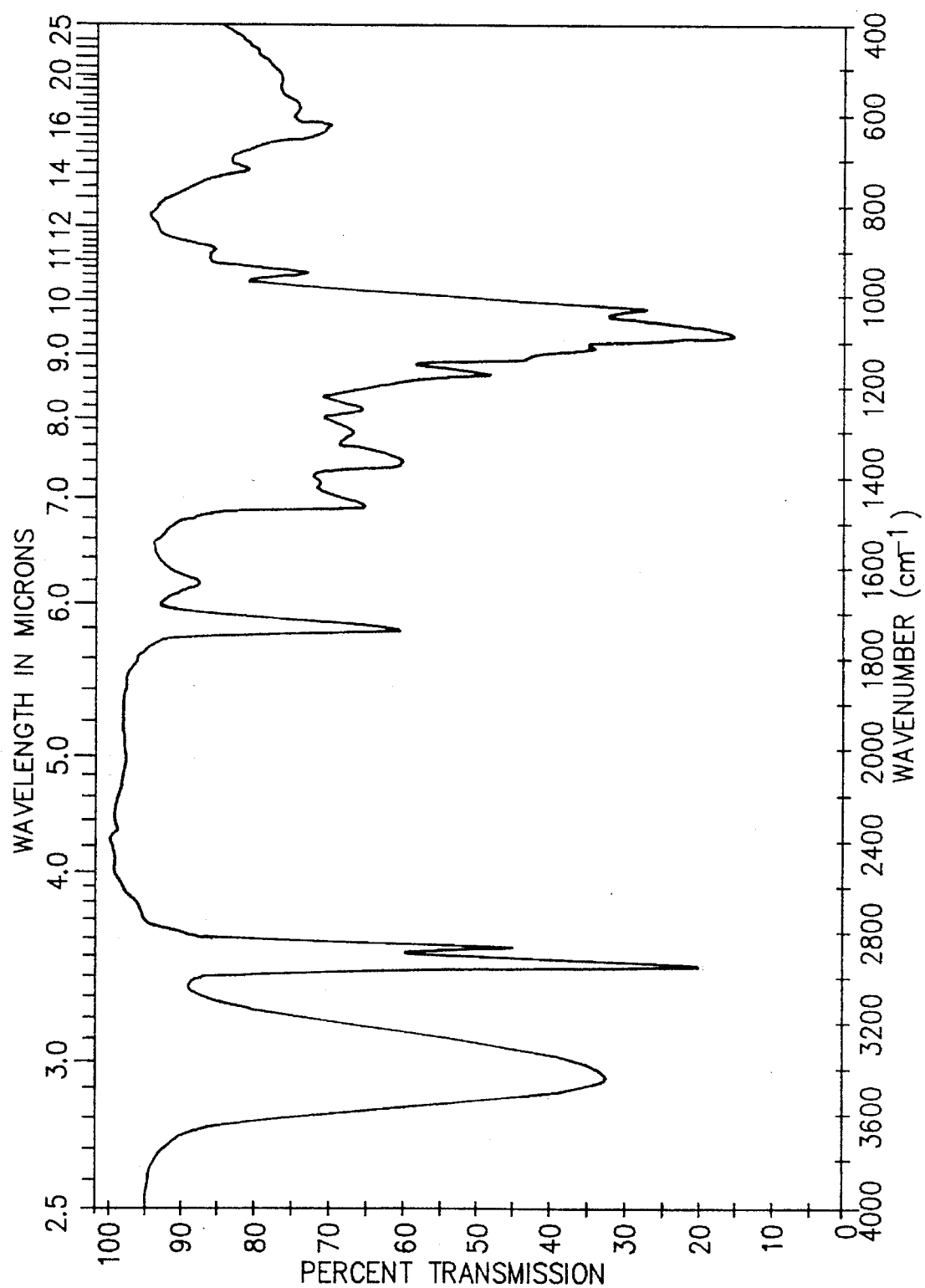
FIG. 2 shows the IR spectra of BU-4224V $B_1$.
Figure 3:
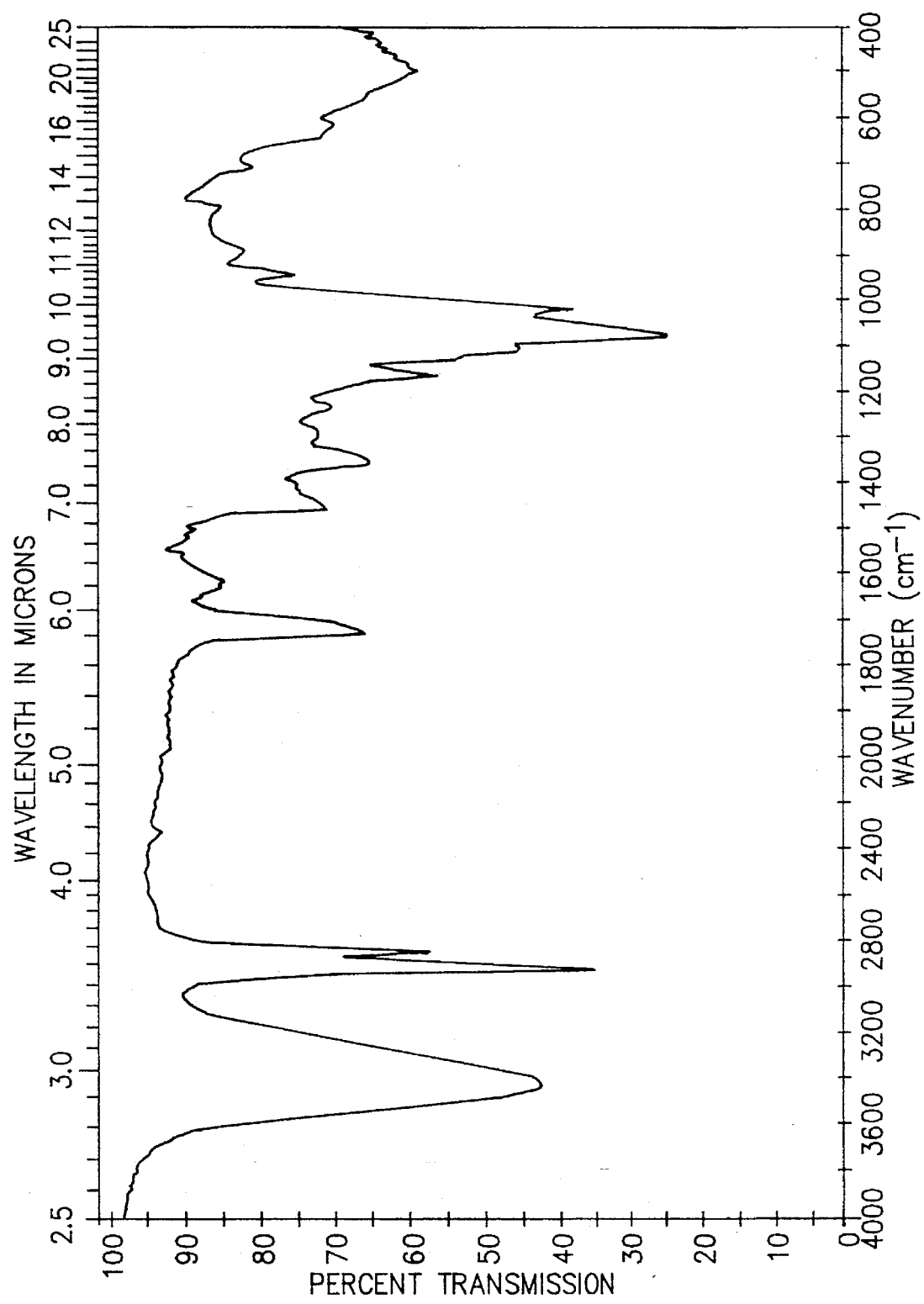
FIG. 3 shows the IR spectra of BU-4224V $B_2$.
Figure 4:
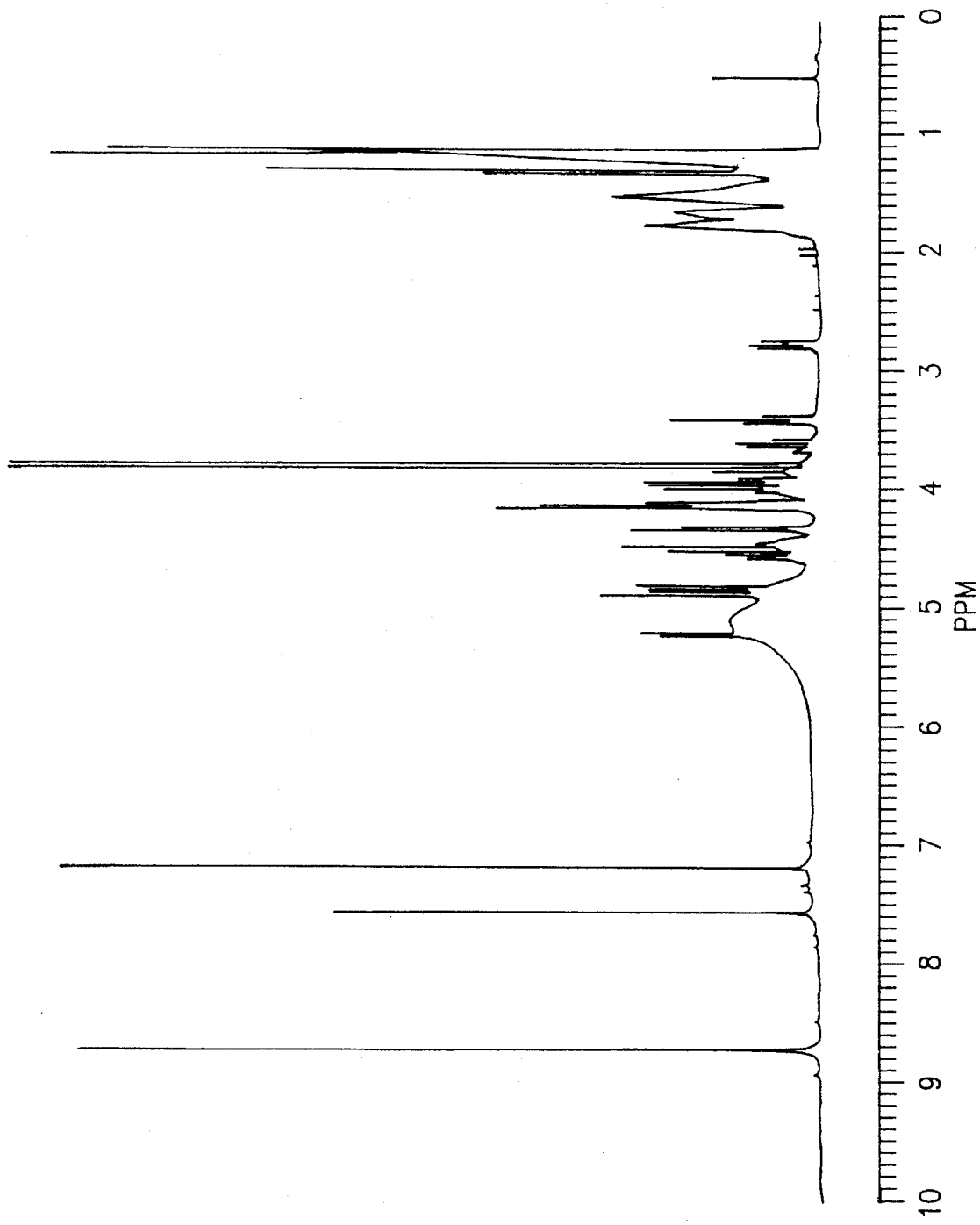
FIG. 4 shows the $^1$H-NMR spectra of BU-4224V $B_1$.
Figure 5:
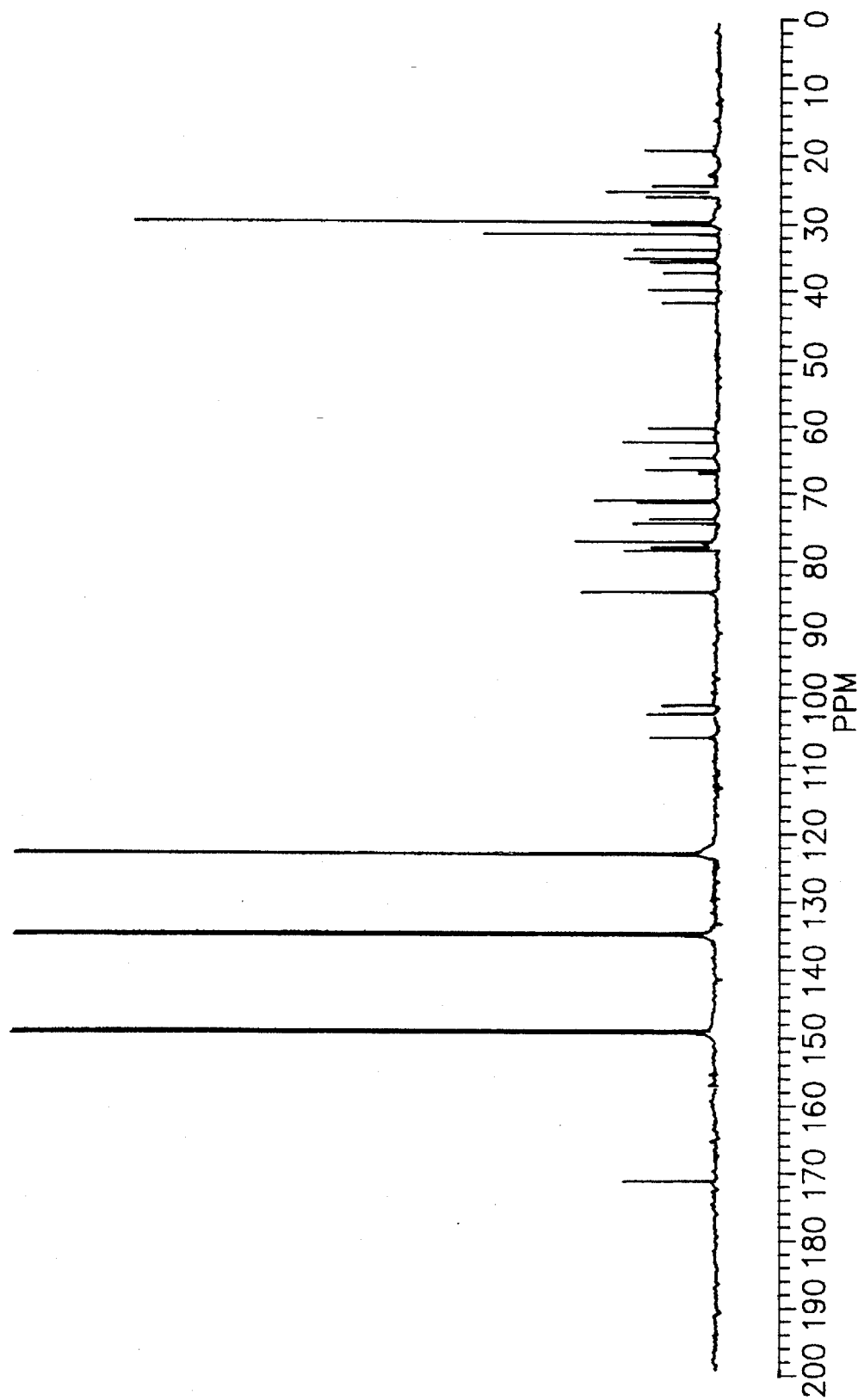
FIG. 5 shows the $^{13}$C-NMR spectra of BU-4224V $B_1$.
Figure 6:
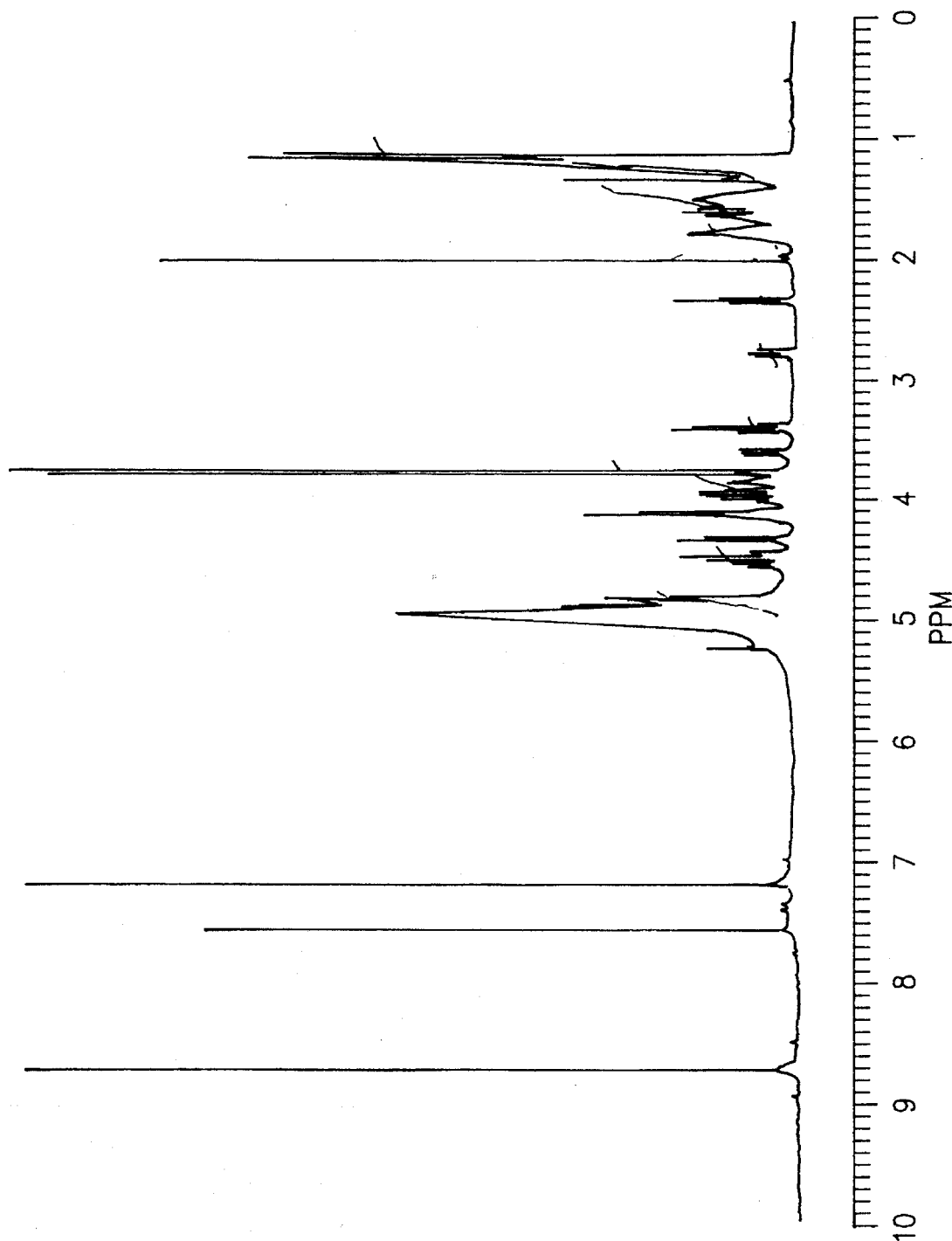
FIG. 6 shows the $^1$H-NMR spectra of BU-4224V $B_2$.
Figure 7:
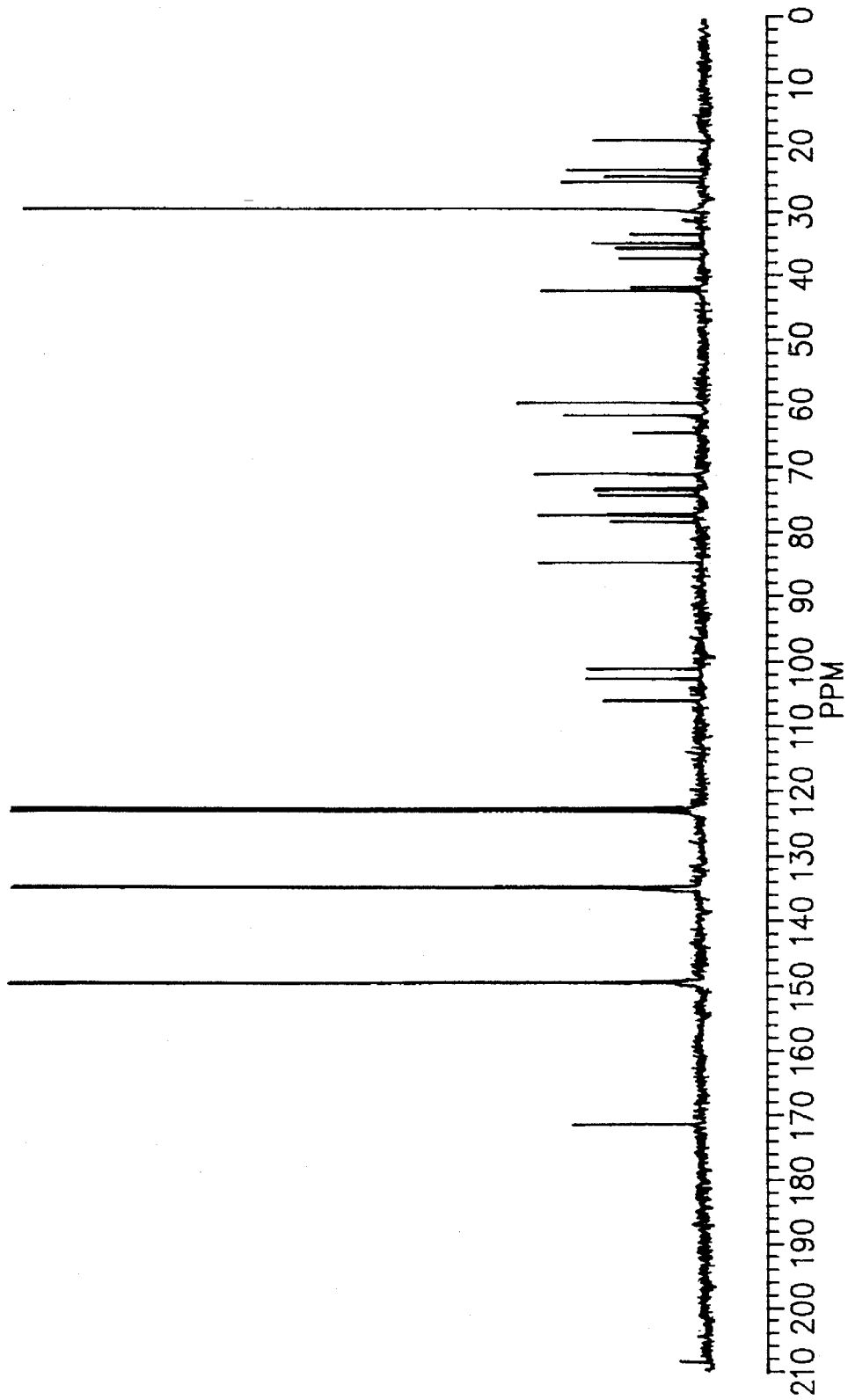
FIG. 7 shows the $^{13}$C-NMR spectra of BU-4224V $B_2$.

BU-4224V $B_1$ and $B_2$ were isolated as a white amorphous powder. They were soluble in methanol, pyridine and dimethyl sulfoxide, slightly soluble in ethyl acetate and acetone but practically insoluble in n-hexane, chloroform and water. They showed positive reactions to iodine and anthrone reagent but were negative to ninhydrin and Sakaguchi tests. The physico-chemical properties of components BU-4224V $B_1$ and $B_2$ are summarized in Table 3. The UV spectra of BU-4224V $B_1$ and $B_2$ showed no absorption maxima above 210 nm. The IR spectra of BU-4224V $B_1$ and $B_2$ are shown in FIGS. 2 and 3, respectively, and their $^1$H-and $^{13}$C-NMR spectra in FIGS. 4–7.

Structure elucidation of BU-4224V $B_1$ and $B_2$

Figure 8:
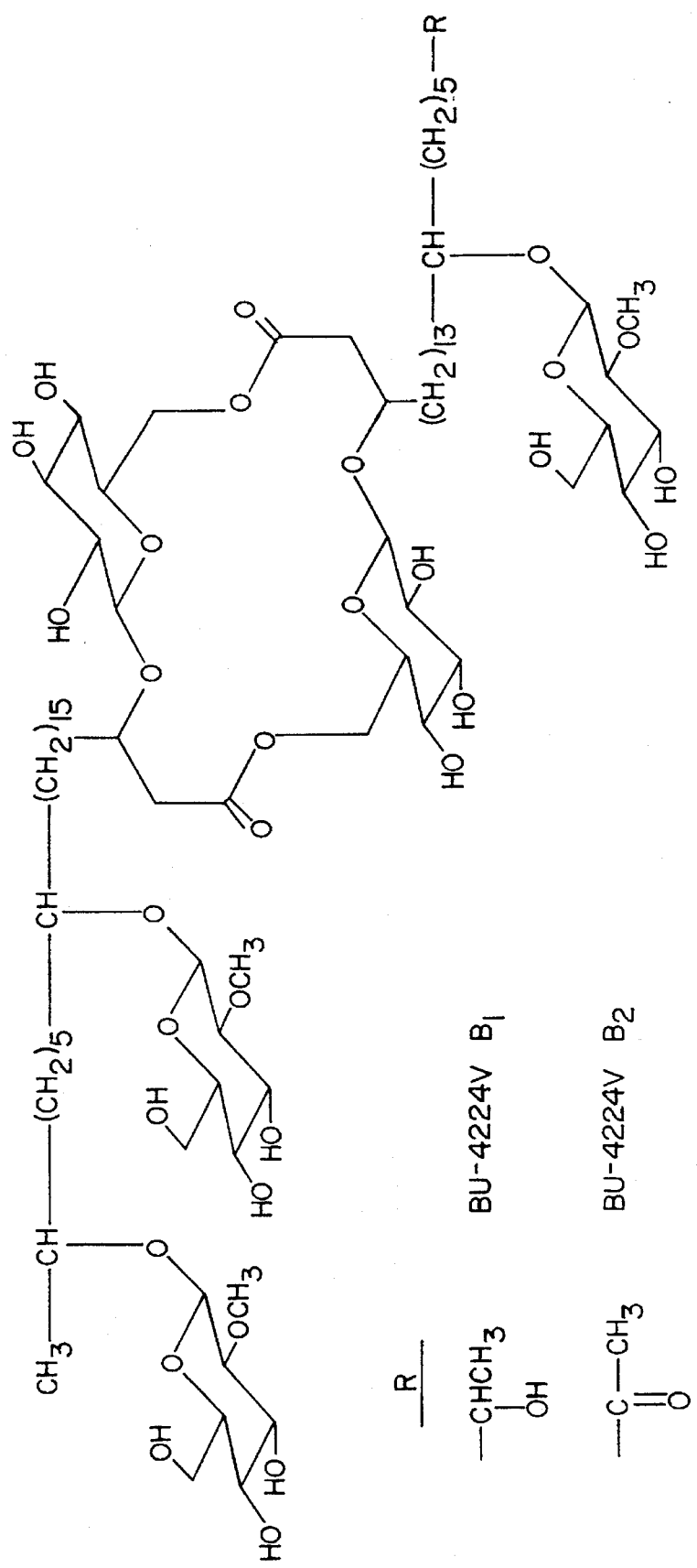
FIG. 8 shows the structures of BU-4224V $B_1$ and $B_2$.

The molecular formulae of BU-4224V $B_1$ and $B_2$ were determined to be $C_{83}H_{152}O_{33}$ and $C_{83}H_{150}O_{33}$, respectively, based on their elemental analyses and negative fast-atom bombardment mass spectral data. The $^1$H-NMR spectrum of $B_1$ showed the presence of five anomeric protons ($\delta$5.23(2H), 4.89, 4.85 & 4.82), three 0-methyl groups ($\delta$3.82(6H) & 3.77), two C-methyl groups ($\delta$1.34 and 1.22) and a large number of C-methylene protons ($\delta$1.1–1.9) (Table 4). The information together with that of the IR and $^{13}$C-NMR spectra suggested that BU-4224V $B_1$ was composed of sugars and long-chain fatty acids. The $^1$H-NMR spectrum of BU-4224V $B_2$ was quite similar to that of BU-4224V $B_1$ except that a doublet of methyl signal ($\delta$1.34) of the latter was absent and a singlet methyl ($\delta$2.03) and a triplet methylene ($\delta$2.36) signals were observed in the former. Comparison of the $^{13}$C-NMR spectra of $B_1$ and $B_2$ substantiated the difference of carbon signals as deduced by the above $^1$H-NMR (Table 5). The complete structures of BU-4224V $B_1$ and $B_2$ (FIG. 8), were elucidated by a combination of chemical degradation experiments and spectral analyses of the products. BU-4224V $B_1$ and $B_2$ contain D-glucoses, 2-methoxy glucoses and hydroxylated long-chain fatty acids.

TABLE 3

Physico-chemical properties of BU-4224V $B_1$ and $B_2$

|  | BU-4224V $B_1$ | BU-4224V $B_2$ |
|---|---|---|
| Nature | White amorphous powder | White amorphous powder |
| M.p. | 84–85° C. | 82–83° C. |
| $[\alpha]_D^{26}$(c 0.5, MeOH) | −15.6° C. | −16.1° C. |
| (−)FAB—MS | m/z 1675 (M-1)$^−$ | m/z 1673 (M-1)$^−$ |
| Mol. wt. | 1676 | 1674 |
| Elemental analysis | $C_{83}H_{152}O_{33}\cdot 2H_2O$ | $C_{83}H_{150}O_{33}\cdot 2H_2O$ |
|  | Calcd. found | Calcd. found |
|  | C 58.18 58.03 | C 58.24 58.15 |
|  | H 9.11 8.99 | H 9.00 8.91 |
| IR (KBr) cm$^{-1}$ | 3410, 2930, 2850 1740, 1640, 1470 1370, 1200–1000 | 3430, 2930, 2850, 1735 1720 (sh.), 1630, 1470 1200–1000 |
| TLC, SiO$_2$ (EtOAc—MeOH—H$_2$O = 10:3:1) | Rf 0.47 | 0.47 |
| TLC, RP-18 (Merck: CH$_3$CN-0.022M phosphate buffer, pH 7.0, 70:30) | Rf 0.30 | 0.33 |
| HPLC (YMC-Pack D-ODS-5, CH$_3$CN-0.022M phosphate buffer, pH 7.0, 60:40) | Rt 8.2 min | 9.2 min |

TABLE 4

$^1$H-NMR data of BU-4224V $B_1$ and $B_2$ (400 MHz, Pyridine-$d_5$)

| BU-4224V $B_1$ | BU-4224V $B_2$ |
|---|---|
| δ 5.23 (2H, br-d, J = 9.4) | δ 5.24 (2H, br-d, J = 9.8) |
| 4.89 (1H, d, J = 7.7) | 4.90 (1H, d, J = 7.7) |
| 4.85 (1H, d, J = 7.7) | 4.85 (1H, d, J = 7.7) |
| 4.82 (1H, d, J = 7.7) | 4.82 (1H, d, J = 8.1) |
| 4.4–4.6 (8H, m) | 4.4–4.6 (8H, m) |
| 4.34 (4H, m) | 4.34 (4H, m) |
| 4.15 (10H, m) | 4.15 (10H, m) |
| 3.9–4.1 (8H, m) | 3.9–4.1 (7H, m) |
| 3.86 (3H, m) | 3.86 (3H, m) |
| 3.82 (6H, s) | 3.82 (6H, s) |
| 3.77 (3H, s) | 3.77 (3H, s) |
| 3.62 (2H, dd, J = 4.7 & 15.4) | 3.62 (2H, dd, J = 4.3 & 15.4) |
|  | 3.42 (3H, q-like, J = 8.6) |
| 3.42 (3H, q-like, J = 8.7) | 2.79 (2H, dd, J = 9.0 & 15.4) |
| 2.79 (2H, dd, J = 9.4 & 15.4) | 2.36 (2H, t, J = 7.3) |
|  | 2.03 (3H, s) |
| 1.1–1.9 (76H, m) | 1.1–1.9 (74H, m) |
| 1.34 (3H, d, J = 6.4) | 1.22 (3H, d, J = 6.0) |
| 1.22 (3H, d, J = 6.4) |  |

TABLE 5

$^{13}$C-NMR data of EU-4224V $B_1$ and $B_2$ (100 MHz, Pyridine-d5)

| Carbon | BU-4224V $B_1$ | BU-4224V $B_2$ |
|---|---|---|
| 1 | δ171.7 s | δ208.1 s |
| 2 | 106.4 d | 171.7 s |
| 3 | 103.1 d | 106.4 d |
| 4 | 101.8 d | 103.1 d |
| 5 | 85.3 d | 101.8 d |
| 6 | 85.0 d | 85.3 d |
| 7 | 79.3 d | 85.1 d |
| 8 | 78.9 d | 79.3 d |
| 9 | 78.3 d | 79.2 d |
| 10 | 78.1 d | 78.9 d |
| 11 | 78.0 d | 78.3 d |
| 12 | 77.7 d | 78.1 d |
| 13 | 77.6 d | 78.0 d |
| 14 | 75.1 d | 77.7 d |
| 15 | 74.5 d | 77.6 d |
| 16 | 74.2 d | 75.1 d |
| 17 | 72.1 d | 74.5 d |
| 18 | 71.8 d | 74.2 d |
| 19 | 71.7 d | 72.1 d |
| 20 | 67.0 d | 71.8 d |
| 21 | 65.3 t | 71.7 d |
| 22 | 62.9 t | 65.4 t |
| 23 | 62.8 t | 62.9 t |
| 24 | 60.7 q | 62.8 t |
| 25 | 60.6 q | 60.8 q |
| 26 | 42.4 t | 60.6 q |
| 27 | 40.1 t | 43.4 t |
| 28 | 37.7 t | 42.4 t |
| 29 | 36.0 t | 37.8 t |
| 30 | 35.3 t | 36.0 t |
| 31 | 34.2 t | 35.4 t |
| 32 | 30.4 t | 34.2 t |
| 33 | 30.3 t | 34.0 t |
| 34 | 30.2 t | 30.4 t |
| 35 | 29.9 t | 30.2 t |
| 36 | 26.4 t | 30.1 t |
| 37 | 25.7 t | 30.0 t |
| 38 | 25.6 t | 29.9 t |
| 39 | 25.2 t | 29.7 t |
| 40 | 24.3 q | 29.6 q |
| 41 | 19.5 q | 25.7 t |
| 42 |  | 25.6 t |
| 43 |  | 25.2 t |
| 44 |  | 24.9 t |
| 45 |  | 24.1 t |
| 46 |  | 19.5 q |

Physico-chemical properties of BU-4224VA and C

Figure 9:
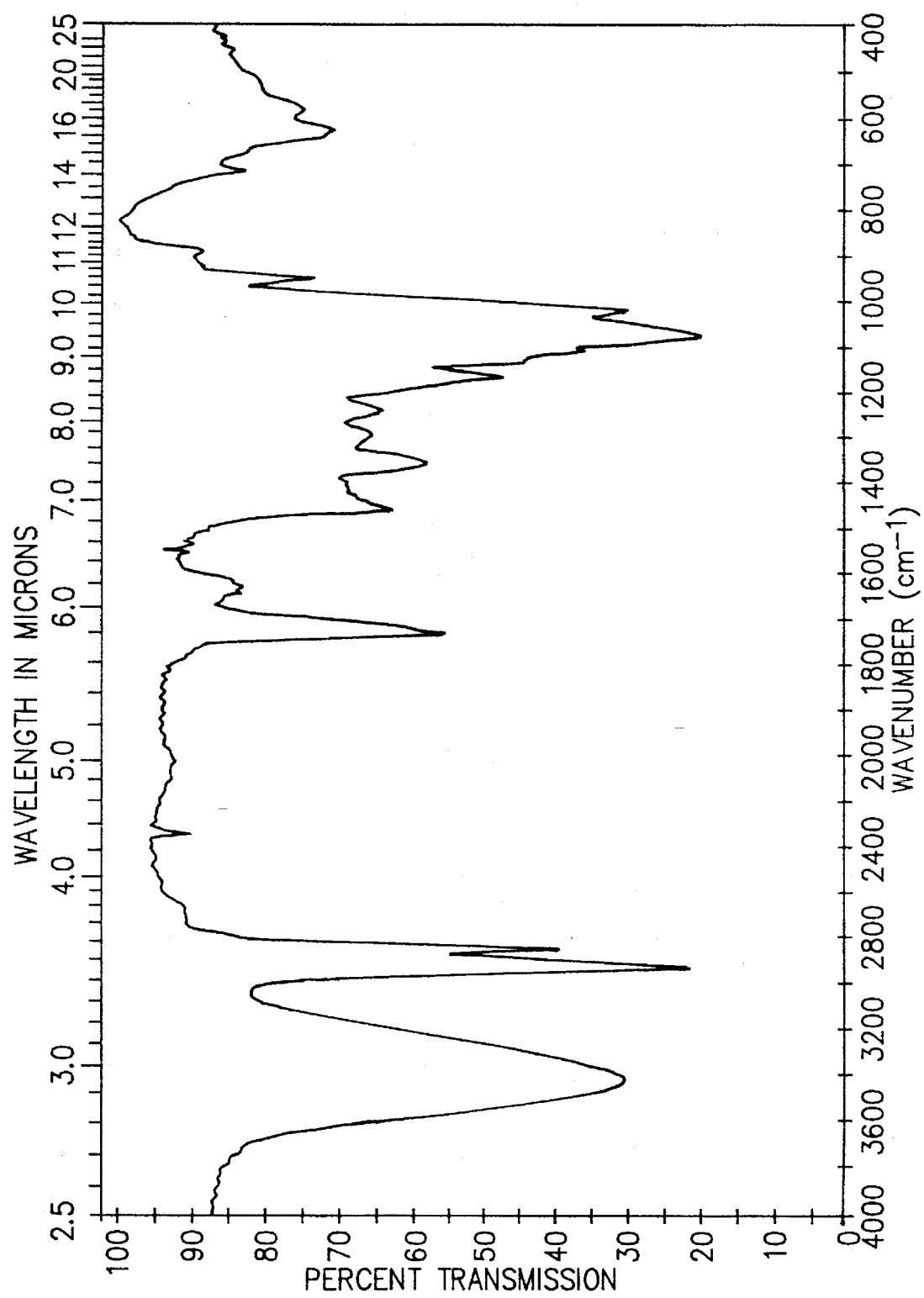
FIG. 9 shows the IR spectra of BU-4224V A.
Figure 10:
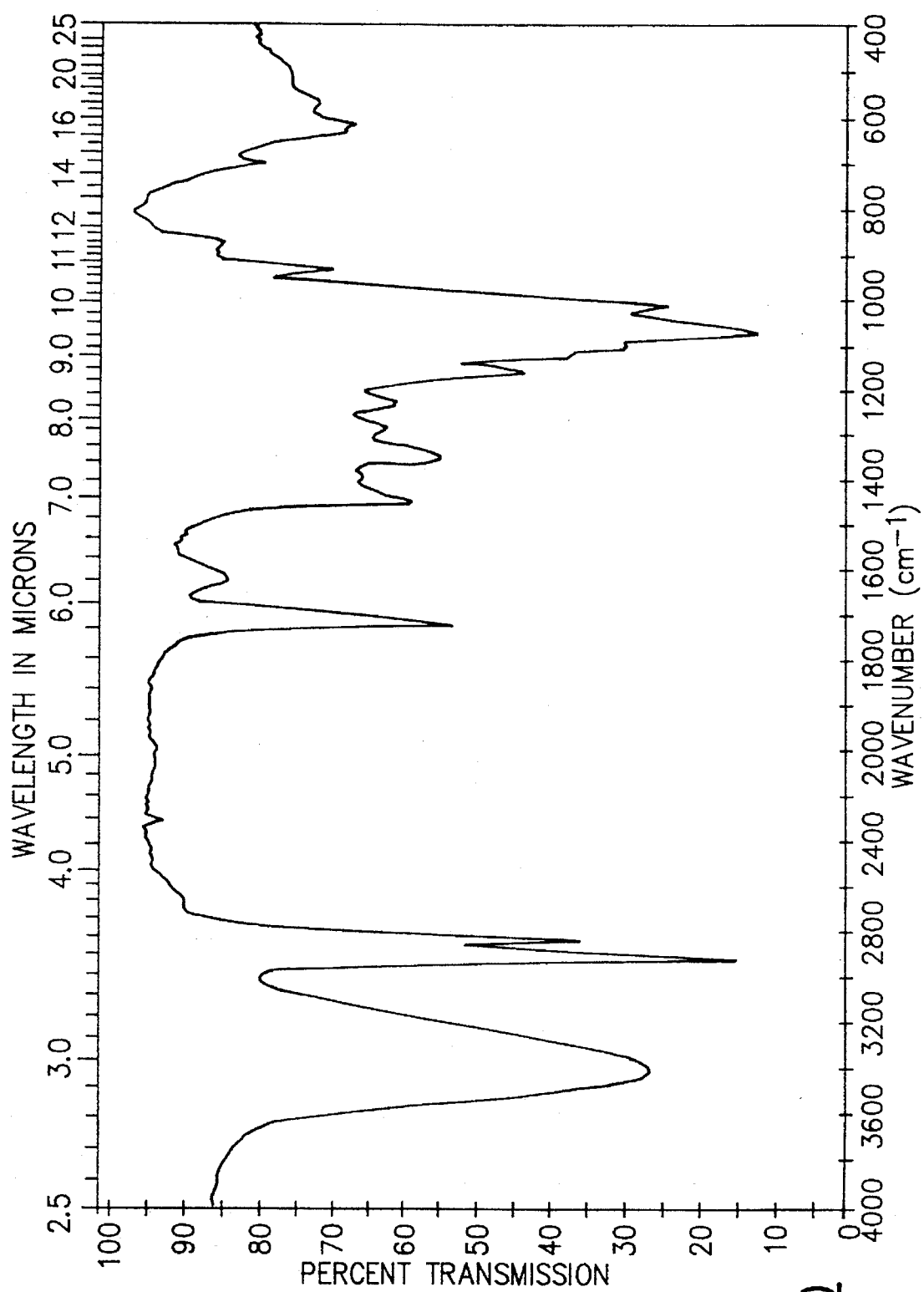
FIG. 10 shows the IR spectra of BU-4224V C.

The components BU-4224V A and C are minor products and found, by HPLC, to consist of two to four subcomponents. Their separation has not been carried out and their structure has not been determined. The physico-chemical properties of BU-4224V A and C are summarized in Table 6 and the IR spectra of BU-4224V A and C are given in FIGS. 9 and FIG. 10, respectively. They have properties similar to those of the major components, BU-4224V $B_1$ and $B_2$.

TABLE 6

Physico-chemical properties of BU-4224V A and C

|  | BU-4224V A | BU-4224V C |
|---|---|---|
| Nature | White amorphous powder | White amorphous powder |
| M.P. | 77–78° C. | 75–77° C. |
| $[\alpha]_D^{25}$(c 0.5, MeOH) | −13° | −20° |
| Negative FAB—MS | m/z 1743, 1683, 1647 | m/z 1731 |
| Elemental analysis | found (%) | found (%) |
|  | C 46.02 | C 57.66 |
|  | H 7.30 | H 8.92 |
| IR (KBr) cm$^{-1}$ | 3410, 2930, 2850, 1735 1720 (sh), 1640, 1460 1360, 1200–1000 | 3400, 2920, 2850, 1735, 1640, 1470, 1360 1200–1000 |
| UV (MeOH) | No absorption maxima above 210 nm | |
| TLC, SiO$_2$ (EtOAc—MeOH—H$_2$O = 10:3:1) | Rf 0.47 | 0.47 |

TABLE 6-continued

Physico-chemical properties of BU-4224V A and C

|  | BU-4224V A | BU-4224V C |
|---|---|---|
| TLC, RP-18 (Merck: CH₃CN-0.022M phosphate buffer, pH 7.0, 70:30) | Rf 0.42 | 0.19 |

Antiviral Activity

Antiviral activity for each component of BU-4224V was evaluated by the dye uptake and the plaque reduction assay using herpes simplex virus type 1 (KOS strain) infection in Vero cells. In the dye uptake assay, 200 µl of the Vero cell suspension containing $1.6 \times 10^4$ cells was poured into each well of 96-well microplates, and then 50 µl of medium containing a test compound at various concentrations was added to each well. The viral suspension (50 µl) containing approximately $30 \times TCID_{50}$ was inoculated to each well. For cytotoxicity tests, the same set of wells without viruses were prepared. After incubation at 37° C. for 72 hours under the humidified 5% $CO_2$-95% air environment, the degree of inhibition of the virus-induced cytopathic effect and the drug-induced cytotoxicity were determined by means of the uptake of neutral red. $ID_{50}$ was expressed as the concentration showing the 50% inhibition of the cytopathic effect of control, and $TD_{50}$ was the concentration exhibiting the 50% cytotoxicity against Vero cells without viral infection. Acyclovir was used as a reference compound of anti-HSV activity. The antiviral activity of BU-4224V was also evaluated by the conventional plaque reduction assay method using a 24-well microplate.

Each component of BU-4224V, except for component A, demonstrated a potent antiviral activity against HSV-1 with $ID_{50}$ values of 2~5 µg/ml by the dye uptake assay. This antiviral activity is less potent than that of acyclovir. In the plaque reduction assay, BU-4224V showed almost the same antiviral activity as in the dye uptake assay.

Among the BU-4224V components the component C showed most potent antiviral activity against herpes simplex virus type 1(HSV-1) in the dye uptake assay and the plaque reduction assay. BU-4224V $B_1$ and $B_2$ were almost at the same level in the above assays and 2–3 times less active than BU-4224V C against HSV-1. Component C exhibited anti-HSV activity with $ID_{50}$ values of 2.3 µg/ml by the dye uptake assay and 2.8 µg/ml by the plaque reduction assay. All of the components exhibited no cytotoxicity ($TD_{50}$:>400 mcg/ml, MDT: >200mcg/ml) against HSV-Vero cells. A summary of the anti-HSV activity of each component of BU-4224V is shown in Table 7.

Antimicrobial Activity

The antimicrobial spectra of BU-4224V $B_1$ and $B_2$ against various bacteria and fungi are shown in Table 8. MICs were determined by the agar dilution method using nutrient agar medium (Eiken) for aerobic bacteria and Sabouraud dextrose agar for fungi. The inoculum size was adjusted to $10^3$–$10^4$ cfu/ml for aerobic bacteria and $10^6$ for fungi.

BU-4224V $B_1$ and $B_2$ exhibited weak antibacterial activity against aerobic Gram-positive bacteria and showed no activity against aerobic Gram-negative bacteria and fungi.

Table 9 shows the antimicrobial activity of BU-4224V A and C. BU-4224V A exhibited weak inhibitory activity only against *Staphylococcus aureus* FDA 209P, Smith, *S. epidermidis* D153 and *Bacillus subtilis* PCI219. BU-4224V C exhibited antimicrobial activity but not at 100 µg/ml.

TABLE 7

Anti-HSV activity of BU-4224V

HSV-Vero cells

|  | Dye uptake assay | | Plaque reduction assay | |
|---|---|---|---|---|
|  | $ID_{50}$ (µg/ml) | $TD_{50}$ (µg/ml) | $ID_{50}$ (µg/ml) | MTD* (µg/ml) |
| BU-4224V A | 15.8 | >400 | 44.1 | >200 |
| BU-4224V $B_1$ | 4.9 | >400 | 10.9 | >200 |
| BU-4224V $B_2$ | 5.0 | >400 | 9.3 | >200 |
| BU-4224V C | 2.3 | >400 | 2.8 | >200 |
| Acyclovir | 0.09 | >100 | 0.27 | >100 |

*MTD: Minimal toxic dose

TABLE 8

Antibacterial activity of BU-4224V $B_1$ and $B_2$

| | MIC (µg/ml) | |
|---|---|---|
| Organism | BU-4224V $B_1$ | BU-4224V $B_2$ |
| *Escherichia coli* NIHJ | >100 | >100 |
| *Klebsiella pneumoniae* D11 | >100 | >100 |
| *Pseudomonas aeruginosa* A9930 | >100 | >100 |
| *Proteus vulgaris* A9436 | >100 | >100 |
| *Staphylococcus aureus* FDA 209P | 12.5 | 50 |
| *Staphylococcus aureus* Smith | 12.5 | 100 |
| *Staphylococcus aureus* D136 | 25 | >100 |
| *Staphylococcus aureus* A15097 | 25 | >100 |
| *Staphylococcus epidermidis* D153 | 3.1 | 6.3 |
| *Streptococcus faecalis* A9612 | >100 | >100 |
| *Micrococcus luteus* 1001 | >100 | >100 |
| *Bacillus subtilis* PCI219 | 3.1 | 6.3 |
| *Candida albicans* IAM4888 | >100 | >100 |
| *Cryptococcus neoformans* IAM4514 | >100 | >100 |
| *Aspergillus fumigatus* IAM2034 | >100 | >100 |
| *Trichophyton mentagrophytes* D155 | >100 | >100 |

TABLE 9

Antimicrobial activity of BU-4224V A and C

| | MIC (µg/ml) | |
|---|---|---|
| Organism | BU-4224V A | BU-4224V C |
| *Escherichia coli* NIHJ | >100 | >100 |
| *Klebsiella pneumoniae* D11 | >100 | >100 |
| *Pseudomonas aeruginosa* A9930 | >100 | >100 |
| *Proteus vulgaris* A9436 | >100 | >100 |
| *Staphylococcus aureus* FDA 209P | 50 | >100 |
| *Staphylococcus aureus* Smith | 100 | >100 |
| *Staphylococcus aureus* D136 | >100 | >100 |
| *Staphylococcus aureus* A15097 | >100 | >100 |
| *Staphylococcus epidermidis* D153 | 12.5 | >100 |
| *Streptococcus faecalis* A9612 | >100 | >100 |
| *Micrococcus luteus* 1001 | >100 | >100 |
| *Bacillus subtilis* PCI219 | 6.3 | >100 |
| *Candida albicans* IAM4888 | >100 | >100 |
| *Cryptococcus neoformans* IAM4514 | >100 | >100 |
| *Aspergillus fumigatus* IAM2034 | >100 | >100 |
| *Trichophyton mentagrophytes* D155 | >100 | >100 |

According to one aspect of the invention, therefore, there is provided a process for the production of antibiotics by fermentation of a BU-4224V-producing strain of *Kibdelosporangium albatum*.

Another aspect of the invention provides a method for therapeutically treating animal and human viral infections by administering to the afflicted host an effective amount of BU-4224V $B_1$, $B_2$, or C, or combinations thereof.

Another aspect of the invention provides a method for therapeutically treating animal and human microbial infections by administering to the afflicted host an effective amount of BU-4224V A, $B_1$, or $B_2$, or combinations thereof.

In yet another aspect of this invention a pharmaceutical composition is provided which comprises an effective amount of BU-4224V A, $B_1$, $B_2$, or C, or combinations thereof, in combination with an inert pharmaceutical acceptable carrier or diluent. These compositions can be made up in any pharmaceutical form appropriate for the desired route of administration.

This invention also provides the microorganism *Kibdelosporangium albatum* having the identifying characteristics of strain No. R761-7, (ATCC 55061).

The pharmaceutical composition provided by the present invention may contain other active ingredients, e.g., other antibiotic agents, and may be made up in any form appropriate for the desired route of administration. Examples of such compositions include solid compositions for oral administration such as capsules, tablets, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or other sterile injectable medium immediately before use.

It will be appreciated that the actual dosages of the compounds of the present invention will vary according to the particular compound being used, the particular composition formulated, the mode of administration and the particular situs, host and disease being treated. Many factors that modify the action of the drug will be taken into account by those skilled in the art, e.g. age, body weight, sex, diet, time of administration, route of administration, rate of excretion, condition of the host, drug combinations, reactions sensitivities and severity of the disease. Optimal dosages for a given set of conditions can be ascertained by those skilled in the art using conventional dosage determination tests.

The following examples are provided for illustrative purposes only and are not intended to limit the scope of the invention.

References

1) Shirling, E. B. & D. Gottlieb: Methods for characterization of Streptomyces species. Int. J. Syst Bacteriol. 16: 313–340, 1966
2) Shearer, M. C. et al.: New genus of the Actinomycetales: *Kibdelosporangium aridum* gen. nov., sp. nov. Int. J. Syst. Bacteriol. 36: 47–54, 1986
3) Lechevalier, M.P.: Identification of aerobic actinomycetes of clinical importance. J. Lab. Clin. Med. 71: 934–944, 1968
4) Lechevalier, M. P.; C. D. Bievre and H. Lechevalier: Chemotaxonomy of aerobic actinomycetes: phospholipid composition. Biochem. Syst. Ecol. 5: 249–260, 1977
5) Collins, M. D.; T. Pirouz, M. Goodfellow and D. E. Minnikin: Distribution of menaquinones in actinomycetes and corynebacteria. J. Gen. Microbiol. 100: 221–230, 1977
6) Minnikin, D. E.; L. Alshamaony and M. Goodfellow: Differentiation of Mycobacterium, Nocardia, and related taxa by thin-layer chromatographic analysis of whole-organism methanolysates. J. Gen. Microbiol. 88: 200–204, 1975
7) Uchida, K. and K. Aida: Taxonomic significance of cell-wall acyl type in Corynebacterium-Mycobacterium-Nocardia group by a glycolate test. J. Gen. Appl. Microbial. 25: 169–183, 1979
8) Lechevalier, M. P., H. Prauser, D. P. Labeda and J. S. Ruan: Two new genera of nocardioform actinomycetes: Amycolata gen. nov. and Amycolatopsis gen. nov. Int. J. Syst. Bacteriol. 36: 29–37, 1986
9) Shearer, M. C. et al.: Aridicins, novel glycopeptide antibiotics. I. Taxonomy, production and biological activity. J. Antibiotics 38: 555–560, 1985
10) Mertz, F. P. and R. C. Yao: *Kibdelosporangium philippinense* sp. nov. isolated from soil. Int. J. Syst. Bacteriol. 38: 282–286, 1988
11) Shearer, M. C. et al.: Kibdelins, novel glycopeptide antibiotics. I. Discovery, production, and biological evaluation. J. Antibiotics 39: 1386–1394, 1986

EXAMPLE I

Fermentation

A small agar piece of the slant culture of *Kibdelosporangium albatum* strain R761-7 was inoculated into a 500-ml Erlenmeyer flask containing 100 ml of the seed medium consisting of mashed potato 4%, corn steep liquor 2%, $CaCO_3$ 0.3% and NaCl 0.2% (the pH was adjusted to 8.0 before autoclaving). The seed culture was incubated at 28° C. for 4 days on a rotary shaker (200 rpm) and 5 ml of the culture was transferred into a 500-ml Erlenmeyer flask containing 100 ml of the production medium having the same composition as the seed medium. The fermentation was carried out at 28° C. for 6 days on a rotary shaker. The antibiotic production in the fermentation broth was monitored by the conventional cytopathic effect (CPE) assay method using herpes simplex virus type I (KOS strain). The production of the complex reached a maximum after 4 to 5 days and the antiviral activity was observed x48 broth dilution in terms of $IC_{50}$ value.

EXAMPLE II

Isolation and purification

The fermentation broth (20 liters, 50–100 µg/ml) was stirred vigorously with n-butanol (8 liters) for 30 minutes. The n-butanol extract was concentrated in vacuo to dryness and the residue (9.0 g) was mixed with silica gel (25 g) and loaded on the top of a silica gel column (Wakogel C-200, 1.1 liters). The column was developed with ethyl acetate-methanol-water (100:15:1) mixture. The eluate was collected in fractions (20 ml) which were examined by the antiviral assay and TLC ($SiO_2$; EtOAc-MeOH-$H_2O$, 10:3:1, $H_2SO_4$ detection). Appropriate fractions were combined and concentrated in vacuo to give a crude mixture solid of BU-4224 V (1.0 g).

The solid (1.0 g) was dissolved in methanol (5 ml) and subjected to reversed phase $C_{18}$ column chromatography (YMC-ODS, AM type, Yamamura Chem. Lab. Co. Ltd., 800 ml). The column was washed with a 0.022 M phosphate buffer solution (pH 7.0) containing 45% $CH_3CN$ (1.5 liters) and then developed with the solution containing 50% $CH_3CN$ (fr. 1–65) and 55% $CH_3CN$ (fr. 66–98). Presence of the antibiotics was detected by TLC (RP-18, Merck: $CH_3CN$-0.022M phosphate buffer, pH 7.0, 70:30). Fraction Nos. 9–15 (Rf. 0.42) were pooled, concentrated and extracted with n-butanol. The n-butanol extract was evaporated in vacuo to afford a white powder of BU-4224V A (98 mg). Fraction Nos. 35–52 (Rf 0.32) and Nos. 62–80 (Rf 0.19) were worked up by the same way to afford white powders of BU-4224V B (330 mg) and BU-4224 V C (140 mg), respectively. The minor components, BU-4224 V A and C were found to consist of 2 to 4 subcomponents by HPLC (FIG. 1). Thus, the major component, BU-4224V B was also revealed to contain two components, BU-4224 V $B_1$ and $B_2$ (FIG. 1). Separation of BU-4224V B mixture (140 mg) was carried out by preparative HPLC (Column: YMC-Pack D-ODS-5, Yamamura Chem. Lab. Co. Ltd., 20×250 mm, mobile phase: $CH_3CN$-0.01M phosphate buffer, pH 7.0, 54:46, detection: UV 210 nm). The first peak cuts containing BU-4224 V $B_1$ were combined and concentrated. The solution was extracted with n-butanol and the extract was evaporated to a white powder of BU-4224 V $B_1$ (54 mg). This solid was chromatographed on a column of Sephadex LH-20 (200 ml) eluting with 90% aqueous methanol to afford a pure sample of BU-4224 V $B_1$ (48 mg). The second peak cuts containing component $B_2$ were worked up by a similar manner to yield a pure solid of BU-4224 V $B_2$ (49 mg).

We claim:

1. The compound BU-4224 V A characterized as follows:
   (a) appearance: white amorphous powder
   (b) melting point: 77°–78° C.
   (c) optical rotation: $[\alpha]_D^{25}$ –13° (c 0.5, MeOH)
   (d) elemental analysis: C, 46.02%, H 7.30%
   (e) secondary ion mass spectrum: m/z 1743, 1683, 1647
   (f) IR (KBr): 3410, 2930, 2850, 1735, 1720(sh), 1640, 1460, 1360, 1200–1000
   (g) thin-layer chromatography: $R_f$=0.47, $R_f$=0.42 (EtOAc-MeOH-$H_2O$=10:3:1)
   (h) UV in MeOH: No absorption maxima above 210 nm.

2. The compound BU-4224V C characterized as follows:
   (a) appearance: white amorphous powder
   (b) melting point: 75°–77° C.
   (c) optical rotation: $[\alpha]_D^{25}$ –20° (c 0.5, MeOH)
   (d) elemental analysis: C, 57.66%, H 8.92%
   (e) secondary ion mass spectrum: m/z 1731
   (f) IR (KBr): 3400, 2920, 2850, 1735, 1640, 1470, 1360, 1200–1000
   (g) thin-layer chromatography: $R_f$=0.47, $R_f$=0.19 (EtOAc-MeOH-$H_2O$=10:3:1 )
   (h) UV in MeOH: No absorption maxima above 210 nm.

3. A method for treating a mammalian host affected by herpes simplex virus type 1, which method comprises administering to said host an effective amount of the compound of claim 2.

4. A pharmaceutical composition comprising an effective amount of a compound of claim 1 or 2 or combinations thereof, together with a pharmaceutical acceptable carrier.

5. A method for treating a mammalian host affected by bacterial infections, which method comprises administering to said host an effective amount of the compound of claim 1.

* * * * *